US00PP22539P2

(12) United States Plant Patent
Kordes

(10) Patent No.: US PP22,539 P2
(45) Date of Patent: Mar. 6, 2012

(54) SHRUB ROSE PLANT NAMED 'KORGOHOWA'

(50) Latin Name: *Rosa hybrida*
Varietal Denomination: KORgohowa

(75) Inventor: Tim-Hermann Kordes, Klein Offenseth-Sparrieshoop (DE)

(73) Assignee: W. Kordes' Söhne Rosenschulen GmbH & Co KG, Offenseth-Sparrieshoop (DE)

( * ) Notice: Subject to any disclaimer, the term of this patent is extended or adjusted under 35 U.S.C. 154(b) by 0 days.

(21) Appl. No.: 12/925,239

(22) Filed: Oct. 14, 2010

(51) Int. Cl.
*A01H 5/00* (2006.01)

(52) U.S. Cl. ..... Plt./104; Plt./102

(58) Field of Classification Search ..... Plt./102, Plt./104, 108, 105
See application file for complete search history.

*Primary Examiner* — Kent L Bell

(57) ABSTRACT

A new and distinct variety of rose with long lasting, novel yellow flowers with red edges, and attractive foliage with good disease resistance. It exhibits uniform growth with abundant flowers. The new variety propagates well from cuttings and by grafting. This new and distinct variety has shown to be uniform and stable in the resulting generations from asexual propagation.

1 Drawing Sheet

Latin name of genus and species: The botanical classification of the new rose plant is *Rosa hybrida.*

Variety denomination: The denomination of the new variety is 'KORgohowa'.

CROSS REFERENCES AND FEDERAL R&D STATEMENT

There are no cross referenced or related applications. This variety was developed without the aid of any research grant.

BACKGROUND OF THE INVENTION

The new variety of rose plant of the present invention originated from a controlled crossing in a breeding program of two distinct parents during the spring of 2001. The crossing was between an unnamed seedling, and another unnamed seedling.

The resulting seeds were planted during the following winter. The resulting seedlings were evaluated and exhibited distinctive physical and biological characteristics. The new rose plant was selected as a single plant from the seedling beds due to its superior characteristics and asexually propagated for further evaluation. This new and distinctive rose variety is named 'KORgohowa'.

SUMMARY OF THE INVENTION

The new rose plant may be distinguished from its seed parent, an unnamed seedling, by the following combination of characteristics:

1. Foliage on 'KORgohowa' is moderately glossy, while foliage on the unnamed seedling is very glossy.
2. 'KORgohowa' has on average 50-60 petals, while the unnamed seedling has, on average, 10-15 petals.

The new rose plant may be distinguished from its pollen parent, an unnamed seedling by the following combination of characteristics:

1. Flower diameter of 'KORgohowa' is 70 mm on average, while flower diameter of the unnamed seedling is 120 mm on average.
2. 'KORgohowa' has on average 50-60 petals, while the unnamed seedling has on average 30-40 petals.

The objective of the hybridization was to create a new and distinct rose plant with unique qualities, such as:

1. Uniform growth and flowering;
2. Abundant attractive, recurrent flowers;
3. Attractive and abundant foliage; and
3. Resistance to diseases encountered in landscapes and gardens.

This combination of qualities is not present in prior rose cultivars known to the inventor. These objectives have been substantially achieved and in that distinguish 'KORgohowa' from all other varieties of which I am aware.

As part of a rose development program, Tim-Hermann Kordes germinated seeds from the aforementioned hybridization and conducted evaluations and observations on the resulting seedlings in a controlled environment in Offenseth-Sparrieshoop, Germany. The resulting seedlings exhibited distinctive physical and biological characteristics. The new rose plant 'KORgohowa' was selected in May, 2002 from the seedling beds to be asexually propagated for further evaluation. The first asexual propagation of 'KORgohowa' was done by budding to seedling understocks in July, 2002 at the inventor's nursery in Offenseth-Sparrieshoop, Germany.

This initial and other subsequent propagations conducted in controlled environments demonstrate that 'KORgohowa' reproduces true to type in successive generations of asexual reproduction.

BRIEF DESCRIPTION OF THE DRAWING

The accompanying color drawing shows as true as is reasonably possible to obtain in color photographs of this type, the typical characteristics of the buds, flowers, leaves, and stems of 'KORgohowa'.

DETAILED BOTANICAL DESCRIPTION

The following is a description of 'KORgohowa', as observed growing in September, 2010 in a nursery in Jackson County, Oreg. on plants of 4 years of age. Color references are made using The Royal Horticultural Society (London, England) Colour Chart, 2001 except where common terms of color are used.

For a comparison, several physical characteristics of the rose variety 'KORresia', a rose variety from the same inventor described and illustrated in U.S. Plant Pat. No. 3,509 and issued on Mar. 5, 1974 are compared to 'KORgohowa' in Chart 1.

CHART 1

| Characteristic | 'KORgohowa' | 'KORresia' |
|---|---|---|
| Petal Count | 50-60 | 17-25 |
| Fragrance | Moderate fragrance | Strong fragrance |
| Plant height | 130-150 cm | 60-75 cm |

Parents:

*Seed parent.*—An unnamed seedling.

*Pollen parent.*—An unnamed seedling.

Classification:

*Botanical classification.—Rosa hybrida,* 'KORgohowa'.

*Commercial classification.*—Shrub rose.

FLOWER AND FLOWER BUD

Blooming habit: Recurrent.

Flower bud:

*Size.*—Upon opening, 25 mm in length from base of receptacle to end of bud and 15 mm diameter at its widest point.

*Bud form.*—Long. Pointed ovoid.

*Bud color.*—As sepals first unfold, bud color is Yellow Group 12B. When ¼ open, the upper surface of petals is Yellow Group 12A, and the lower surface is Yellow-Orange Group 15A.

*Sepals.*—Size: Average 25-30 mm long×10 mm wide. Shape: Sepals generally subulate. Sepal apex is generally cirrose. Moderate foliaceous appendages on three of the five sepals. Base is flat at union with receptacle. Quantity: Five. Margins: With stipitate glands. Surface texture: Inner side: Covered in fine hairs. Outer surface: Smooth. Stipitate glands are present. Color: Upper surface Green Group 138A. Lower surface Green Group N144C.

Receptacle:

*Surface.*—Smooth.

*Color.*—Yellow Group N144C.

*Shape.*—Urn-shaped.

*Size.*—7 mm (h)×10 mm (w).

Peduncle:

*Surface.*—Smooth.

*Length.*—34-45 mm average length.

*Diameter.*—2-4 mm average diameter.

*Color.*—Yellow Group N144D.

*Strength.*—Moderate.

*Borne.*—Singly. 1 - 2 buds per flowering stem.

Flower bloom:

*Fragrance.*—Moderate.

*Duration.*—On the plant 10-12 days. Long lasting. As a cut flower, 6 to 8 days. Senesced petals drop away cleanly.

*Size.*—Medium flowered garden rose. When open, the average flower diameter is 70 mm and the average flower height is 40 mm.

*Form.*—Shape of flower when viewed from the side: Upon opening, upper part: Flat. Upon opening, lower part: Flat. Open flower, upper part: Flattened convex. Open flower, lower part: Flattened convex.

Color:

*Upon opening, petals.*—Outermost petals: Outer Side: The basal zone is Yellow Group 13B. The marginal zone is Red Group 40B. Inner Side: The basal zone is Yellow Group 12B. The marginal zone is Orange-Red Group 30A. Innermost petals: Outer Side: Yellow Group 12A. Inner Side: Yellow Group 12A.

*Upon opening, basal petal spots.*—Basal petal spot, outermost petals: Outer Side: Yellow Group 13A. Inner Side: Yellow Group 13A. Basal petal spot, innermost petals: Outer Side: Yellow Group 13A. Inner Side: Yellow Group 13A.

*After opening, petals.*—Outermost petals: Outer Side: Red Group 40A. Inner Side: Red Group 40A with intonations of Yellow-Orange 14A. Innermost petals: Outer Side: Yellow Group 8A with intonations in the marginal zone of Orange Group 29B. Inner Side: Yellow-Group 8B with intonations in the marginal zone of Orange Group 29C.

*After opening, basal petal spots.*—No distinctive coloration at petal base observed. Variegations: None.

General tonality: On open flower Yellow-Orange Group 23A. No change in the general tonality at the end of the 7$^{th}$ day. Afterwards, general tonality is Yellow-Orange Group 20B.

Petals:

*Petal count.*—Approximately 50-60 petals under normal conditions.

*Petal reflex.*—Petals reflex somewhat.

*Petal edge.*—Entire.

*Petal shape.*—Deltoid. Apex shape is round. Shape of base is deltoid.

*Petal size.*—30 mm long; 30 mm wide.

*Thickness.*—Average.

*Petal arrangement.*—Generally in a regular pattern with overlapping edges.

Petaloids: Present.

*Petaloid count.*—Average of 4-6 per flower.

*Petaloid edge.*—Entire.

*Petaloid texture.*—Smooth.

*Petaloid shape.*—Linear to elliptic.

*Petaloid size.*—Petaloids are 12 mm long and 7 mm wide.

*Petaloid color.*—Color of inner side is Yellow Group 12A. Color of outer side is Yellow Group 12A.

Reproductive organs:

*Pistils.*—Approximately 35-45 present. Stigmas: Location: Slightly superior in position to anthers. Color: Yellow Group 4C. Styles: Length: 12 mm long. Color: Yellow Group 4C. Intonations of Red Group 40A.

*Stamens.*—Approximately 60-65 on average and regularly arranged. Anthers: Size: 2 mm long. Color: Yellow Group 4C. Pollen: Generally present. Color: Yellow-Orange Group 17C. Filaments: Color: Yellow-Orange Group 14B. Length: 5 mm.

THE PLANT

Plant growth: Vigorous. Upright to bushy habit. When grown as a budded nursery plant the average plant height is 130-150 cm and the average plant width is 75-85 cm.

Stems:

*Stem color.*—Young wood: Yellow Group N144D. Older wood: Yellow Group N144C.

*Stem surface.*—Young wood: Smooth. Older wood: Smooth.

Prickles: Present.

*Incidence.*—3-6 per 10 cm of older wood. 5-9 per 10 cm of young wood.

*Size.*—Average length: 13 mm.

*Color.*—Immature prickles: Gray-Red Group 178C. Mature prickles: Gray-Yellow Group 161C. Senescing to Gray-Brown Group N199D.

*Shape.*—Linear.

*Anthocyanin.*—Color: Gray-Red Group 178C.

Leaves and leaflets: Normally 7 leaflets on normal leaves in middle of the stem.

*Venation pattern.*—Pyramidal net pattern.

*Leaf size.*—150 mm (l)×120 mm (w).

*Quantity.*—Abundant.

*Texture.*—Upper side of leaflet: Moderately glossy. Leathery. Under side of leaflet: Matte. Leathery.

*Color, mature foliage.*—Upper Leaf Surface: Green Group 137A. Lower Leaf Surface: Green Group 139C.

*Color, juvenile foliage.*—Upper Leaf Surface: Gray-Purple Group 187B. Intonations of Green Group 137A. Lower Leaf Surface: Gray-Red Group 182B.

*Anthocyanin intonation.*—Present. Greyed-Purple Group 187B. Location: Intonations present on juvenile leaf margins, developing leaves, and peduncles.

Stipules:

*Size.*—25 mm long. 12 mm between the tips of the stipule. Main body of stipule 8 mm in width.

*Shape.*—Longitudinally flanged.

*Stipule color.*—Yellow Group 144A.

*Presence of stipitate glands.*—Present on margins.

*Margins.*—Serrated. With stipitate glands.

Petiole:

*Length.*—25 mm.

*Diameter.*—2 mm.

*Petiole color.*—Yellow Group 144B.

*Underneath.*—A few small prickles underneath.

*Stipitate glands.*—A limited number present on petiole margins.

Petiole rachis:

*Length.*—50 mm.

*Diameter.*—2 mm.

*Color.*—Yellow Group 144B.

*Margins.*—With stipitate glands.

*Prickles.*—A few small prickles underneath.

*Stipitate glands.*—Limited numbers of stipitate glands on margins.

Leaflets:

*Size.*—Average size of the terminal leaflet is 70 mm (l)×35 mm (w).

*Shape.*—Ovate. Base: Ovate. Apex: Acute.

*Margins.*—Serrated.

*Texture.*—Leathery.

Hips/Seed formation: Observed. Size: 20 mm (l)×12 mm (diameter). Color: Yellow Group N144C.

Winter hardiness: To date, the variety has been grown successfully in Zone 5.

Disease resistance: Above average resistance to rust (*P. disciflorum*), blackspot (*Diplocarpon rosae*), and Botrytis (*Botrytis cinerea*) diseases under normal growing conditions.

I claim:

1. A new and distinct variety of rose plant, as described and illustrated herein.

* * * * *

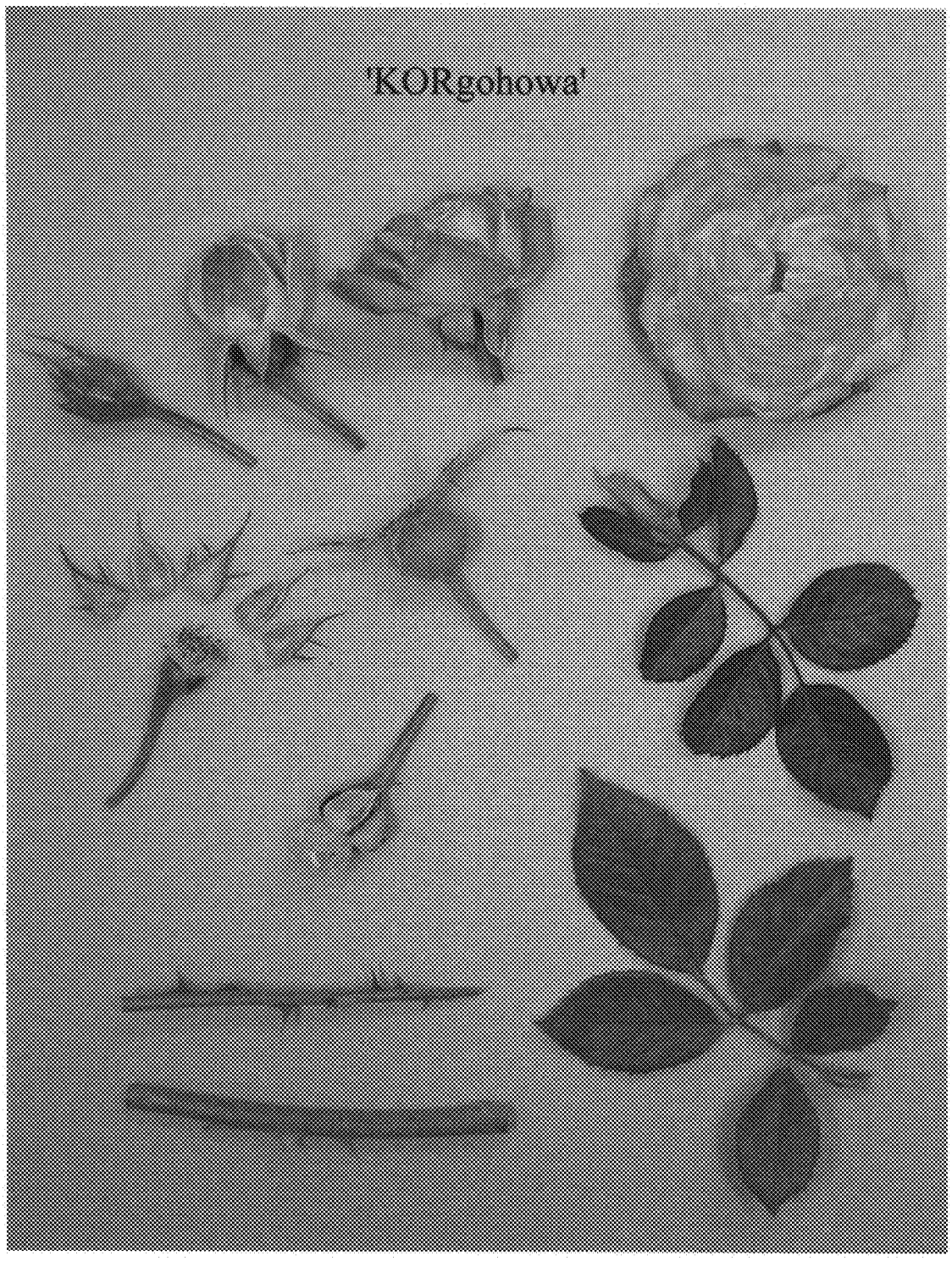
'KORgohowa'